US008809565B2

(12) United States Patent
Oster

(10) Patent No.: US 8,809,565 B2
(45) Date of Patent: Aug. 19, 2014

(54) 5-SULFOISOPHTHALIC ACID SALTS AND PROCESS FOR THE PREPARATION THEREOF

(75) Inventor: Timothy A. Oster, Batesville, AR (US)

(73) Assignee: Futurefuel Chemical Company, Clayton, MO (US)

( * ) Notice: Subject to any disclaimer, the term of this patent is extended or adjusted under 35 U.S.C. 154(b) by 159 days.

(21) Appl. No.: 13/220,465

(22) Filed: Aug. 29, 2011

(65) Prior Publication Data

US 2013/0053593 A1 Feb. 28, 2013

(51) Int. Cl.
*C07F 15/04* (2006.01)

(52) U.S. Cl.
USPC .............. 556/139; 556/45; 556/113; 556/177

(58) Field of Classification Search
USPC ................... 556/113, 139, 177, 45
See application file for complete search history.

(56) References Cited

U.S. PATENT DOCUMENTS

| 4,303,577 | A | * | 12/1981 | Ridgway et al. ............... 524/158 |
|---|---|---|---|---|
| 6,133,382 | A | | 10/2000 | Studholme |
| 6,334,877 | B1 | | 1/2002 | Studholme |
| 6,355,835 | B1 | | 3/2002 | Kulsrestha et al. |
| 6,703,112 | B1 | * | 3/2004 | Farooq et al. ............... 428/195.1 |
| 2002/0169273 | A1 | | 11/2002 | Duan |
| 2004/0006194 | A1 | | 1/2004 | Duan |
| 2004/0242838 | A1 | | 12/2004 | Duan |
| 2007/0088133 | A1 | | 4/2007 | Heater |
| 2007/0208200 | A1 | | 9/2007 | Parker et al. |
| 2010/0275568 | A1 | * | 11/2010 | Chikatsune et al. ............ 57/247 |
| 2010/0298597 | A1 | | 11/2010 | Oster |

FOREIGN PATENT DOCUMENTS

| CN | 1203909 | 1/1999 |
|---|---|---|
| CN | 1673450 | 9/2005 |
| CN | 200610043229 | 8/2006 |
| CN | 200810097895 | 5/2008 |
| CN | 101279940 | 10/2008 |
| CS | 119642 | 8/1966 |
| CS | 157260 | 12/1973 |
| DE | 19382271 | 2/1971 |
| IN | 172789 | 11/1993 |
| IN | WO2009072144 | 6/2009 |
| JP | 48080539 | 10/1973 |
| JP | 51004142 | 1/1976 |
| JP | 1992-247064 | 9/1992 |
| JP | 2004331527 | 11/2004 |
| JP | 2005145836 | 6/2005 |
| WO | WO2011049940 | 4/2011 |

OTHER PUBLICATIONS

Tian; Crystal growth and design; Jul. 27, 2010, 10(9), 3847-3849.*
Zhang; Inorganic Chemistry Communications; Mar. 18, 2010, 13(6), 706-710.*
Li; Crystal growth and design; Apr. 5, 2010, 10(6), 2650-2660.*
Liu; European Journal of Inorganic Chemistry (2008), (7), 1157-1163.*
US Statutory Invention Registration H1760 (Elango, Waradaraj et al.) Nov. 3, 1998.
http://www.xuyechem.com/pages/lisipa.htm (Jun. 15, 2008).
Yu, et al., Synthesis of sodium bis(2-hydroxyethyl) 5-sulfoisophthalate, Huaxue Shijie, 2005, pp. 26-29, vol. 46 Issue 1, China.
Zhao, et al, Synthesis of medium-temperature SIPE, Hecheng Xianwei Gongye, 2001, p. 5-9, vol. 24, Issue 6, China.
Tang, et al., Improvement of the synthetic process of dimethyl 5-sulfoisophthalate sodium salt, Qingdao Keji Daxue Xuebao, Ziran Kexueban 2003, pp. 113-116, vol. 24 Issue 2, China.
Zhang, Production technique for dimethyl sodiosulfoisophthalate, Juzhi Gongyye Bianjibu, 2002, pp. 20-22, vol. 15, Issue 1, China.
Wu, et al., Study on the production of dyeing modifer SIPM for polyester fiber, Hecheng Xianwei Gongye, 1995, pp. 11-13, vol. 18, Issue 2, China.
Wu, et al., Synthesis of dyeing improver for cationic dye dyeable polyester fibers, Dalian Ligong Daxue Xuebao, 1995, pp. 434-436, vol. 35 Issue 3, China.
Jiang, et al., Synthesis of sodium 3,5-dimethoxycarbonyl benzene sulfonate, Huagong Shikan, 2000, pp. 21-23, vol. 14, Issue 5, China.
Zhang, et al., Synthesis of sodium 5-sulfodimethylisophthalate, Jingxi Huagong Bianjibu, 1998, pp. 29-41, vol. 15, Issue 3, China.
Li, et al., Synthesis of sodium dimethyl 5-sulfoisophthalate, Jingxi Huangong Bianjibu, 2003, pp. 50-52, vol. 20, Issue 1, China.

* cited by examiner

*Primary Examiner* — Sudhakar Katakam
*Assistant Examiner* — Pancham Bakshi
(74) *Attorney, Agent, or Firm* — Husch Blackwell LLP

(57) ABSTRACT

This invention relates to methods for the production of sodium, potassium, rubidium, cesium, magnesium, manganese, cobalt, nickel, aluminum, copper (II) and zinc salts of 5-sulfoisophthalic acid. In addition, this disclosure describes new compositions of matter, specifically, the rubidium, manganese, cobalt, nickel, and copper (II) salts of 5-sulfoisophthalic acid. The method utilizes the addition of metals salts to a crude sulfonation solution of 5-sulfoisophthalic acid.

3 Claims, 3 Drawing Sheets

5-SULFOISOPHTHALIC ACID SALTS AND PROCESS FOR THE PREPARATION THEREOF

CROSS REFERENCE TO RELATED APPLICATION

Not applicable.

FIELD OF THE INVENTION

This disclosure relates to the production of salts of derivatives of isophthalic acid. In particular, this disclosure relates to methods for the production of sodium, potassium, rubidium, cesium, magnesium, manganese, cobalt, nickel, aluminum, copper (II) and zinc salts of 5-sulfoisophthalic acid. In addition, this disclosure describes new compositions of matter, specifically, the rubidium, manganese, cobalt, nickel, and copper (II) salts of 5-sulfoisophthalic acid.

BACKGROUND OF THE INVENTION

This disclosure is intended to teach by way of example and not by way of limitation.

The present invention pertains to the fields of polymer chemistry and specialty chemicals. In particular, this invention relates to the production of salt derivatives of 5-sulfoisophthalic acid. Historically, salt derivatives of sulfoisophthalic acid, such as the mono-lithium and mono-sodium salts of 5-sulfoisophthalic acid, are used in the production of dyed nylon fibers among other polymer fibers. More recently, there has been considerable research devoted to developing new salts of 5-sulfoisophthalic acid and exploring their chemical behaviors and potential uses. This application is an example of such research and development.

A short description of the use of known salt derivatives of 5-sulfoisophthalic acid in nylon processes is presented to provide some context for the research and discoveries that underlie the invention.

Many types of nylons exist and are usually differentiated based on the components used to make them. For example, "nylon 6-6" is a term used to identify nylon made by reacting hexamethylene diamine and adipic acid. Both components donate 6 carbons to the polymer chain thus the nylon is designated "6-6".

Nylon fibers, especially those used for carpet fiber, are also classified as to type, depending on the fiber's receptivity to acid dyes and basic or cationic dyes. Cationic dyeable nylon fibers generally exhibit inherent stain resistant properties as compared to other nylon types but traditionally suffered from poorer lightfastness, especially in light shades. This resulted in the under-utilization of cationic dyeable nylon as a carpet fiber. As expected, considerable time, energy, and resources were devoted to finding new and improved methods to enhance the dye absorbing characteristics of cationic dyeable nylon. Over the years, several methods were developed in which very specialized chemicals were added to the fiber production process to impart improved cationic dye-ability to the polymer.

Two such specialized chemicals are the lithium and sodium salts of 5-sulfoisophthalic acid, commonly known as LiSIPA and NaSIPA respectively. It is believed that other metal salts of SIPA may have similar applications or even more valuable applications.

Developing a commercially viable method of manufacture for SIPA salts presents several challenges, one of which is the variability in HSIPA chemistry. As mentioned previously, the lithium and sodium salts of HSIPA are well known in the art. However, HSIPA chemistry is such that one cannot necessarily take a known process for making one salt (e.g., LiSIPA), switch out the metal (e.g., switch to Na), and expect that the process will result in a similar salt product. For example, one can wash a crude NaSIPA product with water but doing the same with LiSIPA will result in lost product. Likewise, washing crude LiSIPA with acetic acid results in a hydrate or anhydrous product whereas washing crude NaSIPA with acetic acid results in a solvate. Also, one metal cation may require a different solvent system than another metal cation In addition, many of the known processes for producing HSIPA salts results in product having high sulfate levels. A high sulfate HSIPA salt can cause problems in polymer processes. For example, LiSIPA salts with accompanying high levels of sulfate are associated with high levels of nylon filament breakage due to sulfate precipitation. Accordingly, HSIPA salts with a low-sulfate composition are of value because they are expected to cause fewer problems in polymer production processes.

Due to these and other problems in the prior art, some of which are disclosed herein, there is a general need for new technology in the arena of salt derivatives of SIPA. There is a need for new salt derivatives that may have improved polymer processing characteristics as compared to known salts. There is a need to produce such salts in a manner that is both efficient and results in low sulfate levels in anticipation of possible use in nylon applications. There is a need for a robust platform process to produce such salts that can be used to manufacture several different types of salts. Furthermore, the process should be suitable for commercialization using equipment currently employed in most SIPA manufacturing processes.

BRIEF SUMMARY OF THE INVENTION

In one aspect, the claimed invention is a process for the preparation of salts of 5-sulfoisophthalic acid. The process may begin with the formation of a solution of 5-sulfoisophthalic acid (HSIPA). The solution of HSIPA is then contacted with a metal cation producing compound to form a reaction mixture. The reaction mixture is then maintained under conditions sufficient to form a metal salt of 5-sulfoisophthalic acid. The metal salt of 5-sulfoisophthalic acid is then isolated from the reaction mixture and washed with acetic acid.

In another aspect, the claimed invention is a composition of matter comprising the reaction product of a solution of 5-sulfoisophthalic acid and a metal cation producing compound wherein the metal cation is selected from the group consisting of rubidium, manganese, cobalt, nickel, aluminum, and copper (II). The invention also encompasses the rubidium, manganese, cobalt, nickel, aluminum, and copper (II) salts of 5-sulfoisophthalic acid.

DETAILED DESCRIPTION

Figure 1:
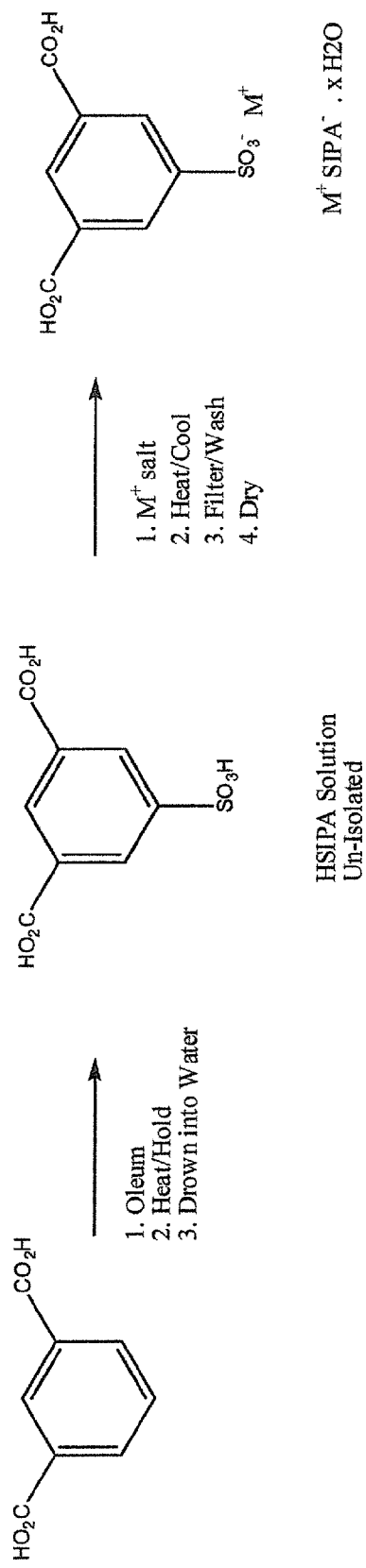
FIG. 1 is a schematic of an exemplary reaction incorporated in the process according to the invention wherein the metal cation is monovalent.

As used herein, the terms "salt of 5-sulfoisophthalic acid", "MtSIPA", and "MtSIPA product" generally, encompass both the hydrated and anhydrous forms of the metal salts discussed herein; the difference being the degree of drying of the final product. Sodium salts are an exception to this. In most instances discussed herein sodium salts SIPA are in the form of a solvate.

As used in this Detailed Description, the term "Mt" when used as a prefix means one of the metals discussed herein. Those metals include sodium, potassium, rubidium, cesium, magnesium, manganese, cobalt, nickel, aluminum, copper (II) and zinc.

As used herein, the term "non-purified" means that the reaction product that leaves the reaction vessel is not subjected to any further substantive processing or purification steps other than filtering and washing. For example, some known processes currently use a "re-crystallization-in-water" step to reduce sulfate levels in the resulting MtSIPA products. The re-crystallization-in-water step is a difficult purification step that reduces overall yields due to the high solubility of some MtSIPA products in water. The process according to the invention avoids the costly "re-crystallization-in-water" and other post-manufacture purification steps.

The term "drowning" as used herein means the addition of one liquid component to another liquid component. In other words, the term means pouring a solution or intermediate slurry into a second liquid.

The method according to the invention in its simplified form comprises the steps of forming a solution containing 5-sulfoisophthalic acid (HSIPA) followed by contacting the solution with a metal cation producing compound to form a reaction mixture (provided the metal cation is not lithium). In preferred embodiments this step of the process comprises forming a sulfonation solution of HSIPA then contacting the sulfonation solution with a metal cation producing compound to form a reaction mixture. The reaction mixture is then maintained under conditions sufficient to form a salt of HSIPA. In some instances this step of maintaining the reaction mixture will comprise heating the reaction mixture to a sufficient temperature for a sufficient period of time to produce a metal salt of 5-sulfoisophthalic acid (MtSIPA). The MtSIPA is then isolated (e.g., filtered) from the reaction mixture. The isolated MtSIPA may then be washed with acetic acid. The washed MtSIPA is then dried and packaged.

Those skilled in the art recognize that the steps outlined above for making MtSIPA can vary considerably in individual industrial processes and vary to some extent based on the metal cation that is utilized. The following paragraphs set forth one possible embodiment of invention. This exemplary embodiment is provided to aid in the understanding of the invention and should not be interpreted as limiting the scope of the invention. Although the invention pertains to the manufacture of MtSIPA, the overall industrial process arguably begins with the production of 5-sulfoisophthalic acid (HSIPA) and this is where the discussion of this exemplary embodiment begins.

Turning now to FIG. 1, isophthalic acid is sulfonated to form HSIPA. There are several known methods for sulfonating isophthalic acid such as combining it with oleum or pure $SO_3$. Any of these known methods of producing HSIPA in an aqueous, dilute sulfuric acid solution are acceptable in the practice of the invention. In this exemplary embodiment isophthalic acid is sulfonated by reacting it with oleum (aka "fuming sulfuric acid") under temperature and time conditions sufficient to form a crude solution of HSIPA in sulfuric acid. In a preferred embodiment the oleum is in solution at a concentration between about 20% and 60% and the sulfonation mixture is heated to a temperature between about 150° C. to about 230° C. for a time sufficient to form HSIPA.

The sulfonation solution of HSIPA is then contacted with a metal cation producing compound to form a reaction mixture. The step of contacting the HSIPA with the metal cation producing compound can occur in several ways. One way of combining the HSIPA with the metal cation is to add an elemental metal directly to a sulfonation mixture. This procedure is typically unsuitable for commercial processes because the resulting reaction often releases substantial quantities of hydrogen gas. Hydrogen gas is explosive therefore safety considerations and the expense of control equipment weigh against this method of combining HSIPA and a metal cation. Other solid metal cation producing compounds can produce similar problems although the severity of the problem varies depending upon the particular metal compound utilized.

Another option for contacting HSIPA with a metal cation producing compound is to combine a solution of crude HSIPA with an aqueous solution containing a metal cation-producing compound to form a reaction mixture. In a preferred embodiment a sulfonation solution of HSIPA is drowned into an aqueous solution containing a metal cation-producing compound to form a reaction mixture. Using the sulfonation solution of HSIPA rather than an isolated HSIPA product improves both the temporal and economic efficiency of the overall process making it very attractive for existing commercial production facilities.

A further alternative for contacting HSIPA with a metal cation producing compound is to drown the sulfonation solution of HSIPA into water then add the metal cation producing compound (e.g., a solid metal salt) to the drowned solution to form the reaction mixture. In other words the metal cation producing compound can be added before or after the drowning step. The phrase "contacting a sulfonation solution of 5-sulfoisophthalic acid with a metal cation producing compound" encompasses both situations. The end result is a reaction mixture that contains HSIPA, a metal cation producing compound, and water. Other substances may be present to the extent they do not disrupt the reactions necessary to form a metal salt of 5-sulfosophthalic acid.

Figure 2:
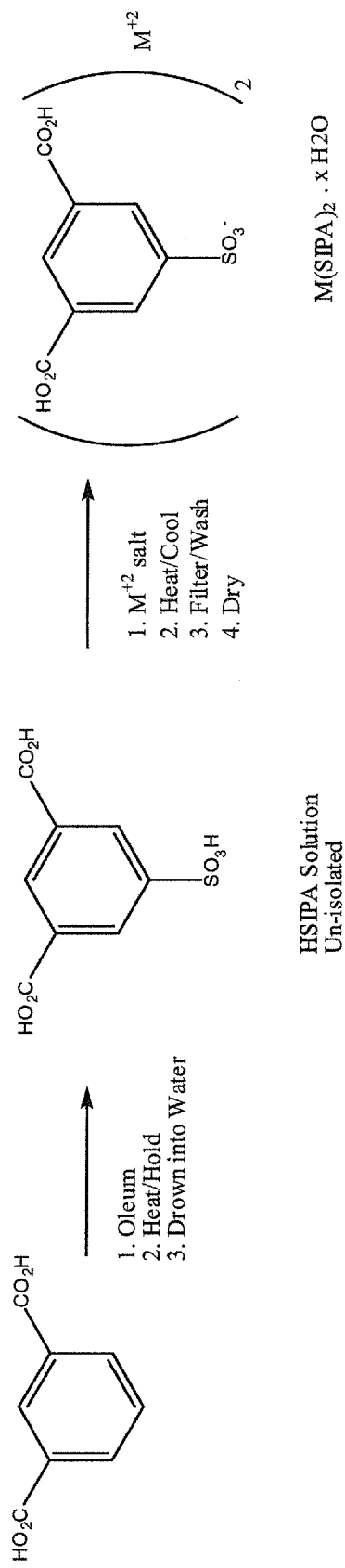
FIG. 2 is a schematic of an exemplary reaction incorporated in the process according to the invention wherein the metal cation is divalent.
Figure 3:
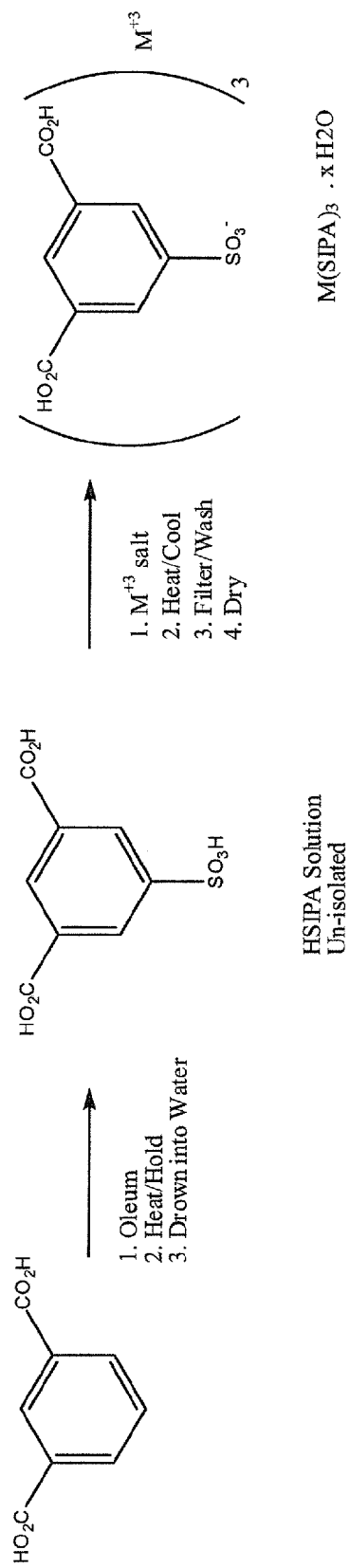
FIG. 3 is a schematic of an exemplary reaction incorporated in the process according to the invention wherein the metal cation is trivalent.

Turning now to FIGS. 1, 2 and 3, the process according to the invention is a very robust process that can be used to form many different MtSIPAs. Metals suitable for use in the present invention include but are not limited to the Group IA metals sodium (NO, potassium ($K^+$), rubidium ($Rb^+$), and cesium ($Cs^+$); the Group 2A metal magnesium ($Mg^{+2}$); the Transition Metals manganese ($Mn^{+2}$) cobalt ($Co^{+2}$), and nickel ($Ni^{+2}$); the Group IB metal copper ($Cu^{+2}$); the Group 2B metal zinc ($Zn^{+2}$); and the Group 3A metal aluminum ($Al^{+3}$).

The metal cation-producing compound may be any of several organic and inorganic compounds capable of producing metal cations in an aqueous solution. In preferred embodiments the metal can take the form of metal hydroxides, organic metal salts such as metal acetates, and inorganic metal salts such as metal carbonates and bicarbonates, metal halides, metal oxides, metal sulfates, or a mixtures of any of these, among other forms. The metal salts can be in their hydrated form (e.g., metal hydroxide monohydrate) or anhydrous forms (e.g., anhydrous metal hydroxides).

The stoichiometry between the metal cation and the HSIPA can vary to some extent. For univalent metals ($Na^+$, $K^+$, $Rb^+$, $Cs^+$) the mole ratio of the metal to HSIPA is ideally 1 to 1 but can be varied between 0.95 to 1 up to 1.05 to 1 or higher, with the cost of the metal compound being the primary limiting factor. For divalent metals ($Mg^{+2}$, $Mn^{+2}$, $Co^{+2}$, $Ni^{+2}$, $Cu^{+2}$, $Zn^{+2}$) the mole ratio of metal to HSIPA can vary between about 0.47 to 1 up to about 0.53 to 1. For trivalent metals ($Al^{+3}$) the mole ratio of metal to HSIPA can vary between about 0.30 to 1 up to 0.35 to 1.

Similarly, the quantity of the reaction mixture and the ratios of the various components of the reaction mixture can vary depending upon the requirements of the particular manufacturing process. In most instances it is anticipated that the process variation employing the drowning step will be the most commercially viable. In such processes the relative amounts of sulfonation solution to aqueous metal cation containing solution can vary greatly. In general, the aqueous portion of the reaction mixture should be sufficient to allow most if not all of the metal cation producing compound to enter into solution under the application of heat (if needed). The reaction mixture is then maintained at reaction conditions sufficient to form a metal salt of HSIPA (i.e., MtSIPA). For those processes where a sulfonation solution is drowned directly into an aqueous solution containing the metal cation, additional heating of the resulting reaction mixture may not be necessary due to the starting temperature of the sulfonation mixture. In most commercial applications of the invention it is anticipated that applying some heat to the reaction mixture will be necessary to achieve solution of the components. The temperature necessary to achieve solution will depend on the concentration of the various components of the reaction mixture and the components themselves. However, it is anticipated that in most commercial applications heating to reflux should be sufficient for all components to go into solution.

The drowning step (and any accompanying heating) to form the reaction mixture may occur very quickly (e.g., in minutes) or over an extended period of time (e.g., hours). The exact time utilized in any particular commercial practice of the invention will be governed in part by the available equipment but times between about 5 minutes and 2 hours are anticipated to be appropriate for most commercial applications. It is recommended that the drowning step be conducted over several minutes for safety, for gradual pH adjustment (if needed), and for thorough mixing of the HSIPA with the metal cation to form the MtSIPA.

The reaction that occurs by contacting the metal cation producing compound with the HSIPA is considered to be virtually instantaneous for those metal compounds that are immediately soluble or are added in a dissolved state. Depending upon the metal used, the reactant ratios, and the temperature of the reaction mixture, a slurry of solid product may form immediately in the reaction mixture. The examples provide information on which of the metals produced precipitating product during developmental work.

The reaction mixture containing the MtSIPA is then cooled. As noted above, depending upon the metal cation utilized in the process, the reaction mixture may contain the product as a solution or as a slurry. For those processes in which the product is in solution, the reaction mixture is cooled to a temperature sufficient to initiate crystallization of the MtSIPA. Typically this temperature is typically between 0° C. and 110° C., with 25° C. being a typical target temperature in commercial processes. The manner of cooling is not critical to the practice of the invention and those skilled in the art are capable of selecting the method most appropriate for their process (e.g., refrigeration). The crystallization step results in a crude MtSIPA that can be separated from the filtrate using any common filtration method, including but not limited to nutsches, centrufuges, autofilter dryers, etc., to form a crude MtSIPA cake.

For those processes in which the product forms a slurry, the reaction mixture is cooled to a temperature sufficient to achieve safe filtering and handling of the product. Typically, this temperature is between 0° and 100° C., with 25° C. being a typical target temperature in commercial processes.

After separation of the crude MtSIPA cake from the reaction mixture filtrate the MtSIPA is washed. Typically, the product is washed with acetic acid. The acetic acid used for the wash is preferably glacial acetic acid but solutions of acetic acid and water may also be used. However, if solutions of acetic acid and water are used the amount of water should be minimized depending upon the metal used because some MtSIPAs are soluble in water and washing with water can result in loss of product. Recycling filtrate and wash streams can reduce product losses resulting from product solubility in water.

Preferably, the acetic acid wash is applied by the method common to the filtration device (e.g., the wash is applied by pumping acetic acid into a nutsche filter). The quantity of acetic acid used is that which is sufficient to be drawn through the MtSIPA cake and displace/remove any remaining filtrate. The wash quantity can be varied from 15% of the weight of the MtSIPA cake to greater than 2 times the weight of the MtSIPA cake. Cost and the ability to recover the acetic acid are the primary constraints limiting the quantity of acetic acid wash used. The temperature of the acetic acid wash typically varies between about 18° C. and 60° C. but can be higher.

After the MtSIPA product is washed it is dried using any appropriate method known to those skilled in the art. In most instances the metal salt can be isolated as an anhydrous solid or as a hydrate depending on the drying conditions (e.g., temperature, time and vacuum).

One of the benefits of the acetic acid wash process is that data collected to date supports the conclusion that the acetic acid does not form a solvate with most MtSIPAs manufactured according to the invention. This is a very surprising discovery considering it is well known that when acetic acid is used as a wash in the production of NaSIPA it forms a solvate with NaSIPA. The NaSIPA/Acetic Acid solvate can be detrimental to polymer end-process (e.g., acetic acid can terminate polymerization). Furthermore, this NaSIPA/acetic acid solvate is very stable. Removal of the acetic acid from the NaSIPA typically requires temperatures in the range of 180° C. under vacuum. Temperatures this high usually result in discolored NaSIPA that is not suitable for use.

In addition to the discovery that acetic acid is an excellent wash for removing residual sulfuric acid from the MtSIPAs (with the exception of the sodium salt), it was surprisingly discovered that under the application of heat and a vacuum during the drying steps, the acetic acid boils off the MtSIPA product prior to the water even though the boiling point of acetic acid is higher than that of water. This allows easy removal of acetic acid while still maintaining a MtSIPA hydrate if the hydrate is the desired end product. If NaSIPA is manufactured in accordance with the invention it is recommended that it not be washed with acetic acid if it is to be used in polymer processes.

Another benefit of using acetic acid as a wash in the MtSIPA process is that it results in a MtSIPA product with less color as compared to other processes that utilize ketones (e.g., acetone, MEK, etc.) as a wash. Washing with ketones allows for the formation of di- and polymeric ketone color bodies. Accordingly, ketone washes are typically followed by a second wash with hexane to remove the ketone, which further increases costs.

As mentioned previously, another benefit seen in the use of acetic acid as a wash is that it substantially reduces the quantity of residual sulfuric in the final product.

In view of the MtSIPA product that is obtained from the above process, the claimed invention also encompasses several metal salts of 5-sulfoisophthalic acid that are made in accordance with the claimed process.

Therefore, another embodiment of the invention comprises the heretofore unknown metal salts of SIPA generated by the process according to the invention. In particular, the invention includes compositions of matter that comprise the reaction product of 5-sulfoisophthalic acid and a metal cation producing compound (such as those described above) wherein the metal cation is selected from the group consisting of rubidium, manganese, cobalt, copper (II), nickel and aluminum. More specifically, the invention includes the following metal salts of 5-sulfoisophthalic acid (HSIPA): the rubidium salt, the manganese salt, the cobalt salt, the nickel salt, the aluminum salt, and the copper (II) salt.

The following examples are provided for purposes of illustration and should not be interpreted as limiting the scope of the invention, which is defined by the claims.

Please note that the presence of the desired product was confirmed both qualitatively and quantitatively. For example, some of the metal salts utilized as reactants have a dark color in their natural state. The disappearance of the dark reactant in the reaction mixture and the known presence of HSIPA followed by the precipitation of product is a qualitative confirmation of the presence of the desired product. In addition, x-ray fluorescence was utilized to confirm the presence of the desired metal in the resulting product. Similarly, liquid chromatography was utilized to confirm the presence of the SIPA moiety in the product.

Example 1

The process according to the invention was utilized to make the potassium salt of 5-sulfoisophthalic acid (NaSIPA).

To a 1000 mL round-bottom flask is added 575 grams of an aqueous HSIPA solution (approximately 28.5% HSIPA and 30% sulfuric acid). Solid KOH (potassium hydroxide, 37.3 grams) was added slowly and the mixture was heated to reflux at about 100 to 120° C. The resulting solution was cooled to crystallize (crystallization occurred at around 84° C.). Four drops of 35% hydrogen peroxide were added and the batch was cooled to 25° C., filtered on a sintered glass funnel and washed twice with glacial acetic acid (70 grams for each wash). The product was dried in a 100° C. vacuum oven to give 143 grams of white solid. The product assayed as follows:

| Weight, grams | 143 |
|---|---|
| Sulfate, % as $SO_4$ | 0.10 |
| Acetate, % as OAc | 0.37 |
| Acidity, % as $H_2SO_4$ | 0.14 |
| Water, % KF | 0.35 |
| SIPA Moiety, LC | Confirmed |
| K, x-ray fluorescence | Confirmed |

Example 2

The process according to the invention was used to make the rubidium salt of 5-sulfoisophthalic acid (RbSIPA).

To a 1000 mL round-bottom flask is added 575 grams of HSIPA solution (approximately 28.5% HSIPA and 30% sulfuric acid). A solution of RbOH (50% rubidium hydroxide, 136.3 grams) was added slowly and the mixture was heated to reflux at about 100 to 120° C. The resulting solution was cooled to crystallize (crystallization occurred at around 63.5° C.). Four drops of 35% Hydrogen Peroxide were added and the batch was cooled to 25° C., filtered on a sintered glass funnel and washed twice with glacial acetic acid (70 grams for each wash). The product was dried in a 100° C. vacuum oven to give 159.7 grams of white solid. The product assayed as follows:

| Weight, grams | 159.7 |
|---|---|
| Sulfate, % as $SO_4$ | 0.01 |
| Acetate, % as OAc | 0.83 |
| Acidity, % as $H_2SO_4$ | 0.83 |
| Water, % KF | 0.10 |
| SIPA Moiety, LC | Confirmed |
| Rb, x-ray fluorescence | Confirmed |

Example 3

The process according to the invention was used to make the cesium salt of 5-sulfoisophthalic acid (CsSIPA).

To a 1000 mL round-bottom flask is added 450 grams of HSIPA solution (approximately 24.3% HSIPA and 23.1% sulfuric acid). A solution of CsOH. H2O (Cesium hydroxide monohydrate, 74.6 grams) was added slowly and the mixture was heated to reflux at about 100° C. to 120° C. The resulting solution was cooled to crystallize (crystallization occurred at around 37.5° C.). Four drops of 35% Hydrogen Peroxide were added and the batch was cooled to 25° C., filtered on a sintered glass funnel and washed twice with glacial acetic acid (70 grams for each wash). The product was dried in a 100° C. vacuum oven to give 67.1 grams of white solid. The product assayed as follows:

| Weight, grams | 67.1 |
|---|---|
| Sulfate, % as $SO_4$ | <0.01 |
| Acetate, % as OAc | 0.02 |
| Acidity, % as $H_2SO_4$ | 0.47 |
| Water, % KF | 0.36 |
| SIPA Moiety, LC | Confirmed |
| Cs, x-ray fluorescence | Confirmed |

Example 4

The process according to the invention was used to make the magnesium salt of 5-sulfoisophthalic acid ($Mg(SIPA)_2$).

To a 1000 mL round-bottom flask is added 575 grams of HSIPA solution (approximately 28.5% HSIPA and 30% sulfuric acid). Solid $MgSO_4$ (magnesium sulfate, 40.0 grams) was added slowly and the mixture was heated to reflux at about 100 to 120° C. The resulting solution was cooled to crystallize (crystallization occurred at around 105 C). Four drops of 35% Hydrogen Peroxide were added and the batch was cooled to 25° C., filtered on a sintered glass funnel and washed twice with glacial acetic acid (70 grams each wash). The product was dried in a 100° C. vacuum oven to give 143 grams of white solid. The product assayed as follows.

| Weight, grams | 143 |
|---|---|
| Sulfate, % as SO4 | 0.16 |
| Acetate, % as OAc | 0.13 |
| Acidity, % as $H_2SO_4$ | 1.08 |
| Water, % KF | 10.2 |
| SIPA Moiety, LC | Confirmed |
| Mg, X-ray fluorescence | Confirmed |

Example 5

The process according to the invention was used to make the manganese salt of 5 sulfoisophthalic acid ($Mn(SIPA)_2$).

To a 1000 mL round-bottom flask is added 575 grams of HSIPA solution (approximately 28.5% HSIPA and 30% sulfuric acid). Solid $Mn(OAc)_2 \cdot 4H_2O$ (manganese acetate tetrahydrate, 81.5 grams) was added slowly and the mixture was heated to reflux at about 100 to 120° C. The resulting solution was cooled to crystallize (crystallization occurred at around 74 C). Four drops of 35% Hydrogen Peroxide were added and the batch was cooled to 25° C., filtered on a sintered glass funnel and washed twice with glacial acetic acid (70 grams each wash). The product was dried in a 100° C. vacuum oven to give 124.1 grams of white solid. The product assayed as follows:

| | |
|---|---|
| Weight, grams | 124.1 |
| Sulfate, % as $SO_4$ | 0.26 |
| Acetate, % as OAc | 0.07 |
| Acidity, % as $H_2SO_4$ | <0.02 |
| Water, % KF | 6.34 |
| SIPA Moiety, LC | Confirmed |
| Mn, X-ray fluorescence | Confirmed |

Example 6

The process according to the invention was used to make a cobalt salt of 5 sulfoisophthalic acid ($Co(SIPA)_2$).

To a 1000 mL round-bottom flask is added 575 grams of HSIPA solution (approximately 28.5% HSIPA and 30% sulfuric acid). Solid $Co(OAc)_2 \cdot 4H_2O$ (Cobalt acetate tetrahydrate, 82.8 grams) was added slowly and the mixture was heated to reflux at about 100 to 120° C. The resulting solution was cooled to crystallize (crystallization occurred at around 68.5° C.). Four drops of 35% Hydrogen Peroxide were added and the batch was cooled to 25 C, filtered on a sintered glass funnel and washed twice with glacial acetic acid (70 grams each wash). The product was dried in a 100° C. vacuum oven to give 133.6 grams of pink solid. The product assayed as follows:

| | |
|---|---|
| Weight, grams | 133.6 |
| Sulfate, % as $SO_4$ | 0.04 |
| Acetate, % as OAc | 0.07 |
| Acidity, % as $H_2SO_4$ | 0.1 |
| Water, % KF | 10.46 |
| SIPA Moiety, LC | Confirmed |
| Co, X-ray fluorescence | Confirmed |

Example 7

The process according to the invention was used to make the nickel salt of 5 sulfoisophthalic acid ($Ni(SIPA)_2$).

To a 1000 mL round-bottom flask is added 450 grams of HSIPA solution (approximately 24.3% HSIPA and 23.1% sulfuric acid). Solid $NiSO_4 \cdot 6H_2O$ (nickel sulfate hexahydrate, 58.4 grams) was added slowly and the mixture was heated to reflux at about 100° C. to 120° C. The resulting solution was cooled to crystallize (crystallization occurred at around 50° C.). Four drops of 35% Hydrogen Peroxide were added and the batch was cooled to 25° C., filtered on a sintered glass funnel and washed twice with glacial acetic acid (70 grams each wash). The product was dried in a 100° C. vacuum oven to give 79.2 grams of light green solid. The product assayed as follows:

| | |
|---|---|
| Weight, grams | 79.2 |
| Sulfate, % as $SO_4$ | 0.06 |
| Acetate, % as OAc | 0.22 |
| Acidity, % as $H_2SO_4$ | 0.03 |
| Water, % KF | 6.66 |
| SIPA Moiety, LC | Confirmed |
| Ni, X-ray fluorescence | Confirmed |

Example 8

The product according to the invention was used to make the copper (II) salt of 5 sulfoisophthalic acid ($Cu(SIPA)_2$).

To a 1000 mL round-bottom flask was added 575 grams of HSIPA solution (approximately 28.5% HSIPA and 30% sulfuric acid). Solid $CuSO_4 \cdot 5H_2O$ (copper sulfate pentahydrate, 83.0 grams) was added slowly and the mixture was heated to reflux at about 100 to 120° C. The resulting solution was cooled to crystallize (crystallization occurred at around 112° C.). Four drops of 35% Hydrogen Peroxide were added and the batch was cooled to 25° C., filtered on a sintered glass funnel and washed twice with glacial acetic acid (70 grams each wash). The product was dried in a 100° C. vacuum oven to give 176.0 grams of light blue solid. The product assayed as follows:

| | |
|---|---|
| Weight, grams | 176.0 |
| Sulfate, % as $SO_4$ | 0.17 |
| Acetate, % as OAc | 0.02 |
| Acidity, % as $H_2SO_4$ | 0 |
| Water, % KF | 8.65 |
| SIPA Moiety, LC | Confirmed |
| Cu, X-ray fluorescence | Confirmed |

Example 9

The process according to the invention was used to make the zinc salt of 5 sulfoisophthalic acid ($Zn(SIPA)_2$).

To a 1000 mL round-bottom flask was added 900 grams of HSIPA solution (approximately 26.5% HSIPA and 34% sulfuric acid). Solid ZnO (zinc oxide, 39.5 grams) was added slowly and the mixture was heated to reflux at about 100° C. to 120° C. About 75 grams of water was distilled out and the resulting solution was cooled to crystallize (crystallization occurred at around 93.5° C.). Two drops of 35% Hydrogen Peroxide were added and the batch was cooled to 25° C., filtered on a sintered glass funnel and washed twice with glacial acetic acid (80 grams each wash). The product was dried in a 100° C. vacuum oven to give 208.0 grams of white solid. The product assayed as follows:

| | |
|---|---|
| Weight, grams | 208 |
| Sulfate, % as $SO_4$ | 0.05 |
| Acetate, % as OAc | 0.06 |
| Acidity, % as $H_2SO_4$ | 0 |
| Water, % KF | 6.35 |
| SIPA Moiety, LC | Confirmed |
| Zn, X-ray fluorescence | Confirmed |

Example 10

The process according to the invention was used to make the aluminum salt of 5 sulfoisophthalic acid ($Al(SIPA)_3$).

To a 1000 mL round-bottom flask was added 575 grams of HSIPA solution (approximately 28.5% HSIPA and 30% sulfuric acid). Solid Al(OH)$_3$ (aluminum hydroxide, 17.3 grams) was added slowly and the mixture was heated to reflux at about 100° C. to 120° C. The resulting solution was cooled to crystallize (crystallization occurred at around 55.5° C.). Four drops of 35% Hydrogen Peroxide were added and the batch was cooled to 25° C., filtered on a sintered glass funnel and washed twice with glacial acetic acid (70 grams each wash). The product was dried in a 100° C. vacuum oven to give 126.0 grams of white solid. The resulting product was estimated to be about 50% Al(SIPA)$_3$ with the remainder being a mixture of HSIPA, sulfuric acid, and water.

| | |
|---|---|
| Weight, grams | 126.0 |
| Sulfate, % as SO4 | 5.01 |
| Acetate, % as OAc | nr |
| Acidity, % as H$_2$SO$_4$ | 19.6 |
| Water, % KF | 6.42 |
| SIPA Moiety, LC | Confirmed |
| Al, X-ray fluorescence | Confirmed |

Example 11

The process according to the invention was used to make the sodium salt of 5 sulfoisophthalic acid (NaSIPA).

To a 1000 mL round-bottom flask is added 450 grams of an aqueous HSIPA solution (approximately 29.12% HSIPA and 29.9% sulfuric acid). Caustic (NaOH, 50%, 42.6 grams) was added slowly and the mixture was heated to reflux at about 100 to 120° C. The resulting slurry was cooled to 85° C. Four drops of 35% hydrogen peroxide were added and the batch was cooled to 25° C., filtered on a sintered glass funnel and washed twice with glacial acetic acid (70 grams for each wash). The product was dried in a 100° C. vacuum oven to give 140.9 grams of white solid. The product assayed as follows:

| | |
|---|---|
| Weight, grams | 140.9 |
| Sulfate, % as SO4 | 0.02 |
| Acetate, % as OAc | 6.16 |
| Acidity, % as H$_2$SO$_4$ | 0.05 |
| Water, % KF | 0.14 |
| SIPA Moiety, LC | Confirmed |
| Al, X-ray fluorescence | Confirmed |

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A composition of matter, said composition of matter comprising the reaction product of a sulfonation solution containing 5-sulfoisophthalic acid and a rubidium cation producing compound.

2. A composition of matter, said composition of matter comprising the reaction product of a sulfonation solution containing 5-sulfoisophthalic acid and a metal cation producing compound wherein said metal cation is selected from the group consisting of manganese, cobalt, nickel, and aluminum.

3. A composition of matter, said composition of matter comprising the reaction product of a sulfonation solution containing 5-sulfoisophthalic acid and a metal cation producing compound wherein said metal cation is copper (II).

* * * * *